US009771312B2

(12) United States Patent
Beckers et al.

(10) Patent No.: US 9,771,312 B2
(45) Date of Patent: Sep. 26, 2017

(54) PROCESS FOR THE CO-PRODUCTION OF ACETIC ACID AND DIMETHYL ETHER

(71) Applicant: BP CHEMICALS LIMITED, Sunbury-on-Thames Middlesex (GB)

(72) Inventors: Mareike Beckers, East Yorkshire (GB); Timothy Crispin Bristow, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 0 days.

(21) Appl. No.: 15/311,939

(22) PCT Filed: Jun. 12, 2015

(86) PCT No.: PCT/EP2015/063141
§ 371 (c)(1),
(2) Date: Nov. 17, 2016

(87) PCT Pub. No.: WO2015/193179
PCT Pub. Date: Dec. 23, 2015

(65) Prior Publication Data
US 2017/0096382 A1  Apr. 6, 2017

(30) Foreign Application Priority Data
Jun. 20, 2014 (EP) .................... 14173352
Jun. 20, 2014 (EP) .................... 14173355

(51) Int. Cl.
C07C 51/09 (2006.01)
C07C 29/80 (2006.01)
C07C 41/09 (2006.01)
C07C 41/16 (2006.01)
C07C 67/54 (2006.01)
C07C 51/44 (2006.01)
C07C 41/42 (2006.01)

(52) U.S. Cl.
CPC .............. *C07C 51/09* (2013.01); *C07C 29/80* (2013.01); *C07C 41/09* (2013.01); *C07C 41/16* (2013.01); *C07C 41/42* (2013.01); *C07C 51/44* (2013.01); *C07C 67/54* (2013.01)

(58) Field of Classification Search
CPC ................. C07C 51/09; C07C 41/42
See application file for complete search history.

(56) References Cited

U.S. PATENT DOCUMENTS

| 4,692,219 A | 9/1987 | Berg | |
| 4,792,620 A * | 12/1988 | Paulik | B01J 31/0231 560/232 |
| 4,802,956 A * | 2/1989 | Dornhagen | B01D 3/14 203/42 |
| 5,227,029 A | 7/1993 | Berg et al. | |

FOREIGN PATENT DOCUMENTS

| EP | 0 124 078 A1 | 11/1984 |
| EP | WO 2011/027105 A1 * | 3/2011 |
| WO | WO 2011/027105 A1 | 3/2011 |
| WO | WO 2013/124404 A1 | 8/2013 |
| WO | WO 2013/124423 A1 | 8/2013 |
| WO | WO 2014/029672 A1 | 2/2014 |

OTHER PUBLICATIONS

Norskov et al, Nature Chemistry, Towards the Computational Design of Solid Catalysts, 2009, 1, pp. 37-46.*

* cited by examiner

*Primary Examiner* — Paul A Zucker
(74) *Attorney, Agent, or Firm* — Nixon & Vanderhye P.C.

(57) ABSTRACT

Process for the co-production of acetic acid and dimethyl ether with reduced formic acid content by distilling a mixture containing dimethyl ether, methanol and methyl formate, separating methyl formate from the mixture to recover dimethyl ether and methanol, and catalytically reacting the methanol and methyl acetate to produce a reaction product of acetic acid an dimethyl ether.

19 Claims, 3 Drawing Sheets

PROCESS FOR THE CO-PRODUCTION OF ACETIC ACID AND DIMETHYL ETHER

This application is the U.S. national phase of International Application No. PCT/EP2015/063141 filed Jun. 12, 2015 which designated the U.S. and claims priority to European Patent Application Nos. 14173355.0 filed Jun. 20, 2014 and 14173352.7 filed Jun. 20, 2014, the entire contents of each of which are hereby incorporated by reference.

The present invention relates to processes for the co-production of acetic acid and dimethyl ether from methanol and methyl acetate feedstocks and, in particular to processes for the co-production of acetic acid and dimethyl ether from methanol and methyl acetate with improved acetic acid purity.

BACKGROUND OF THE INVENTION'

Processes for the co-production of acetic acid and dimethyl ether may be carried out by the catalytic dehydration and hydrolysis of mixtures of methanol and methyl acetate. Such co-production processes are known from, for example WO 2011/027105, WO 2013/124404 and WO 2013/124423.

WO 2011/027105 describes a process for the production of acetic acid and dimethyl ether by contacting methanol and methyl acetate with a catalyst composition at a temperature in the range 140 to 250° C. wherein the catalyst composition contains a zeolite having a 2-dimensional channel system comprising at least one channel which has a 10-membered ring.

WO 2013/124404 describes a process for the co-production of acetic acid and dimethyl ether from a mixture of methanol and methyl acetate by contacting the mixture at a temperature from 200 to 260° C. with a catalyst composition comprising a zeolite possessing a 2-dimensional channel system comprising at least one channel having a 10-membered ring and a silica:alumina molar ratio of at least 22.

WO 2013/124423 describes a process for the production of acetic acid and dimethyl ether by contacting a mixture of methanol and methyl acetate with a zeolite catalyst wherein the zeolite has a 2-dimensional channel system comprising at least one channel having a 10-membered ring and having at least 5% of its cation exchange capacity occupied by one or more alkali metal cations.

Although water is produced in such co-production processes via the dehydration of methanol, a water feed can also be supplied to the process.

In general, methanol is synthesised by converting gaseous mixtures of carbon monoxide, hydrogen and optionally carbon dioxide in the presence of a catalyst, typically a catalyst containing copper as the catalytically active component to produce a crude methanol product. As a result of side-reactions low levels of methyl formate may be produced in the methanol synthesis process.

In processes for the co-production of acetic acid and dimethyl ether, the presence of methyl formate in one or both of the methanol and methyl acetate feedstocks is undesirable as it results in the generation of formic acid which is difficult to separate from acetic acid by conventional fractional distillation techniques owing to the closeness of their boiling points. Instead more complex extractive distillation methods have been employed to achieve acetic acid product purities. Complex methods of this type for the separation of formic acid from acetic acid are described in, for example U.S. Pat. No. 4,692,219 and U.S. Pat. No. 5,227,029.

SUMMARY OF THE INVENTION

Thus, there remains a need for a process for the co-production of acetic acid and dimethyl ether from methanol and methyl acetate in which the purity of acetic acid is improved, and in particular a process in which acetic acid product has a reduced content of formic acid.

Accordingly, the present invention provides a process for the co-production of acetic acid and dimethyl ether which process comprises:

(a) purifying a mixture of dimethyl ether, methanol, water and methyl formate by:
  (i) feeding the mixture of dimethyl ether, methanol, water and methyl formate to a distillation column;
  (ii) distilling the feed mixture of dimethyl ether, methanol, water, formic acid and methyl formate to generate a heads stream depleted in methyl formate as compared to the feed mixture, a base stream depleted in methyl formate as compared to the feed mixture and comprising methanol and water and a sidedraw stream enriched in methyl formate as compared to the feed mixture;
  (iii) withdrawing from the column the sidedraw stream enriched in methyl formate at a point above the feed point of the feed mixture to the column.
(b) feeding at least part of the base stream comprising methanol and water together with methyl acetate to a dehydration-hydrolysis reaction and dehydrating methanol and hydrolysing methyl acetate therein in the presence of at least one solid acid catalyst to produce a crude reaction product comprising acetic acid and dimethyl ether;
(c) recovering acetic acid and dimethyl ether from the crude reaction product.

In step (a) of the process of the present invention the feed mixture to the distillation column comprising dimethyl ether, methanol, water and methyl formate is suitably derived as a crude product stream from a dehydration process to produce dimethyl ether from methanol, such as a catalytic dehydration process, for example dehydration in the presence of a zeolite catalyst. Thus, suitably the feed mixture to the distillation column comprising dimethyl ether, methanol, water and methyl formate is obtained by the steps of:

(I) dehydrating a methanol feed comprising predominantly methanol together with small amounts of methyl formate to form a dehydration product comprising dimethyl ether, water, methanol, formic acid and a reduced amount of methyl formate; and
(II) separating formic acid from the dehydration product to form a mixture comprising dimethyl ether, methanol, water and methyl formate.

Accordingly, the present invention further provides a process for the co-production of acetic acid and dimethyl ether which process comprises:

(I) dehydrating a methanol feed comprising predominantly methanol together with small amounts of methyl formate to form a dehydration product comprising dimethyl ether, water, methanol, formic acid and a reduced amount of methyl formate;
(II) separating formic acid from the dehydration product to form a mixture comprising dimethyl ether, methanol, water and methyl formate;
(a) (i) feeding the mixture comprising dimethyl ether, methanol, water and methyl formate to a distillation column;

(ii) distilling the feed mixture of (i) to generate a heads stream depleted in methyl formate as compared to the feed mixture a base stream depleted in methyl formate as compared to the feed mixture and comprising methanol and water and a sidedraw stream enriched in methyl formate as compared to the feed mixture;

(iii) withdrawing from the column the sidedraw stream enriched in methyl formate at a point above the feed point of the feed mixture to the column.

(b) feeding at least part of the base stream comprising methanol and water together with methyl acetate to a dehydration-hydrolysis reaction and dehydrating methanol and hydrolysing methyl acetate therein in the presence of at least one solid acid catalyst to produce a crude reaction product comprising acetic acid and dimethyl ether;

(c) recovering acetic acid and dimethyl ether from the crude reaction product.

The separation step (II) may be carried out by distillation methods, for example by fractional distillation, in one or more distillation columns, preferably in a single distillation column.

In some or all embodiments of the present invention the crude reaction product in step (b) comprising acetic acid and dimethyl ether has a formic acid content of 500 ppm wt or less.

BRIEF DESCRIPTION OF THE DRAWINGS

The invention is further described with reference to the accompanying drawings, in which.

DETAILED DESCRIPTION OF THE INVENTION

Figure 1:
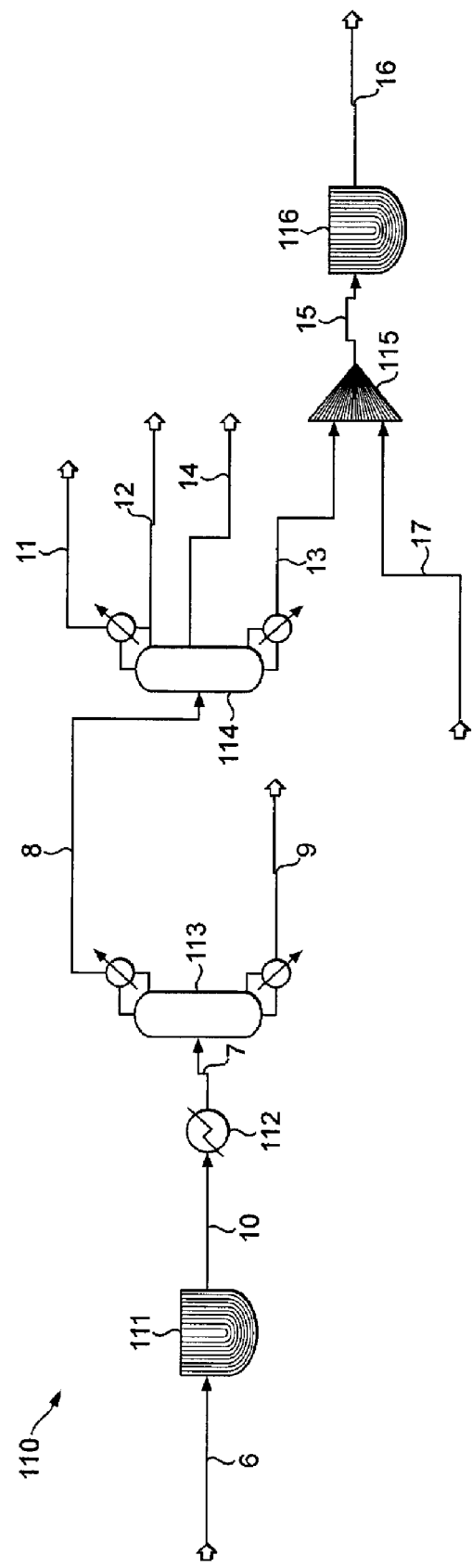
FIG. 1 is a schematic diagram illustrating an embodiment of the present invention for the co-production of acetic acid and dimethyl ether in which methyl formate is removed therefrom.

In step (I) a methanol feed comprising predominantly methanol but also containing small amounts of methyl formate is dehydrated to form a dehydration product comprising dimethyl ether, water, methanol, formic acid and a reduced amount of methyl formate.

Methanol feeds comprising predominantly methanol and small amounts of methyl formate include those produced by catalytically converting a mixture of carbon monoxide and hydrogen and optionally carbon dioxide according to the overall equation $CO + 2H_2 \rightleftharpoons CH_3OH$. The reaction proceeds in accordance with the following reactions:

$$CO_2 + 3H_2 \rightleftharpoons CH_3OH + H_2O \quad (I)$$

$$H_2O + CO \rightleftharpoons CO_2 + H_2 \quad (II)$$

Mixtures of carbon monoxide and hydrogen for methanol synthesis may be obtained from synthesis gas generated, for example from conventional steam reforming or partial oxidation processes. Synthesis gas supplied to a methanol synthesis process may, in addition to carbon monoxide and hydrogen, include carbon dioxide. Small quantities of methyl formate are generated in the methanol synthesis process via side reactions occurring in the synthesis process.

A methanol synthesis process is usually carried out in the presence of a catalyst. A number of catalysts active for methanol synthesis are known in the art and are also available commercially. Typically, such methanol synthesis catalysts comprise copper as an active catalytic component and may also contain one or more additional metals such as zinc, magnesium and aluminium. Examples of methanol synthesis catalysts include, but are not limited to, catalysts comprising zinc oxide and alumina as the support with copper as the active catalytic component.

The methanol synthesis catalyst may be employed in a fixed bed, for example in the shape of pipes or tubes, where the mixture of carbon monoxide and hydrogen is passed over or through the catalyst.

In general, methanol synthesis is carried out at a temperature of from 210° C. to 300° C. and at a total pressure of from 25 to 150 barg (2500 to 15,000 kPa).

In some or all embodiments of the present invention, the methanol feed to step (I) is derived from the production of methanol by the catalytic conversion of a mixture of carbon monoxide and hydrogen, and optionally carbon dioxide, preferably a synthesis gas. The catalyst employed in the production of methanol may be a methanol synthesis catalyst comprising copper as an active catalytic component.

Suitably, in the present invention, a methanol feed to dehydration step (I) comprises methanol in an amount of 50 mol % or greater, for example in an amount 50 to 99 mol %, preferably in an amount of 80 mol % or greater, for example 80 to 99 mol % methanol.

A methanol feed to dehydration step (I) contains methyl formate and may contain methyl formate in an amount of 1 mol % or less, such as 0.5 mol % or less, for example 0.3 mol % or less, such as 0.1 to 1 mol %, for example 0.3 to 1 mol %.

In one or more embodiments of the present invention, the methanol feed to dehydration step (I) comprises 50 to 99 mol %, for example 80 to 99 mol % methanol and >0 to 1 mol %, for example 0.1 to 0.5 mol % methyl formate.

A methanol feed to dehydration step (I) may further comprise one or both of dimethyl ether and water.

Suitably the methanol feed contains water in an amount >0 to 35 mol %, for example 5 to 20 mol %.

The methanol feed may also contain small amounts of dimethyl ether, for example in an amount of 10 mol % or less.

The methanol feed may also contain small amounts of carbon oxides and hydrogen.

In one or more embodiments of the present invention, the methanol feed to dehydration step (I) comprises 50 to 99 mol %, for example 80 to 99 mol % methanol, >0 to 35 mol %, for example 5 to 20 mol % water, 0 to 10 mol % dimethyl ether and >0 to 1 mol % methyl formate.

The methanol feed may be dehydrated in vapour or liquid form. Where a methanol feed comprises liquid phase components, the liquid components may, if desired, be volatilised, for example using a pre-heater.

The dehydration step (I) may be carried out in the presence of any suitable catalyst which is effective to dehydrate methanol to form dimethyl ether and water. Useful catalysts include solid acid catalysts including aluminas such as gamma-alumina and fluorinated alumina, acidic zirconias, aluminium phosphate, silica-alumina supported tungsten oxides.

Suitably, the dehydration step (I) is carried out in the presence of at least one solid Brønsted acid catalyst selected from one or more of heteropolyacids and salts thereof and aluminosilicate zeolites, preferably one or more zeolites.

By 'Brønsted acid catalyst' is meant an acid catalyst which has the ability to donate an acidic proton to facilitate a chemical reaction.

The term "heteropolyacid" as used herein and throughout this specification is meant to include the free acids. Heteropolyacids for use herein may be used either as free acids or as partial salts. Typically, the heteropolyacid, or the anionic component of its corresponding salt comprises 2 to 18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for example cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well-known anions are named after the original researchers in this field and are known, for example as Keggin, Wells-Dawson and Anderson-Evans-Perloff structures.

Heteropolyacids usually have a high molecular weight, for example in the range from 700-8500 and include dimeric complexes. They have a relatively high solubility in polar solvents such as water or other oxygenated solvents, especially if they are free acids and in the case of several salts, and their solubility can be controlled by choosing the appropriate counter-ions. Specific examples of heteropolyacids that may be usefully utilised in the present invention include the free acids such as silicotungstic acids, phosphotungstic acids and 12-tungstophosphoric acid ($H_3[PW_{12}O_{40}]$·$xH_2O$); 12-molybdophosphoric acid ($H_3[PMo_{12}O_{40}]$·$xH_2O$); 12-tungstosilicic acid ($H_4[SiW_{12}O_{40}]$·$xH_2O$); 12-molybdosilicic acid ($H_4[SiMo_{12}O_{40}]$·$xH_2O0$ and ammonium salts of heteropolyacids, such as ammonium salts of a phosphotungstic acid or a silicotungstic acid.

Particularly useful zeolites include those zeolites having a 2-dimensional or 3 dimensional channel system and possess at least one channel which has a 10-membered ring. Specific non-limiting examples of such zeolites include zeolites of framework type FER (typified by ferrierite and ZSM-35), MFI (typified by ZSM-5), MFS (typified by ZSM-57), HEU (for example clinoptilolite) and NES (typified by NU-87).

Suitably, the zeolite further comprises at least one channel having an 8-membered ring. Non-limiting examples include zeolites of framework type selected from FER, HEU and MFS.

The three-letter codes such as 'FER' refer to the framework structure type of the zeolites using the nomenclature proposed by the International Zeolite Association. Information about structure codes and zeolites is available in the Atlas of Zeolite Framework Types, C. H. Baerlocher, L. B. Mccusker and D. H. Olson, 6th Revised Edition, Elsevier, Amsterdam, 2007 and is also available on the website of the International Zeolite Association at www.iza-online.org.

A zeolite utilised in the dehydration step (I) may be employed in an exchanged form. Exchanged forms of zeolites can be prepared by techniques such as ion-exchange and impregnation. These techniques are well-known and typically involve the exchange of the hydrogen or ammonium cations of a zeolite with metal cations. For example, in the present invention, the zeolite may be in an exchanged form with one or more alkali metal cations for example sodium, lithium, potassium and cesium. Suitable exchanged form zeolites include ferrierite and ZSM-35 exchanged with one or more of sodium, lithium, potassium and cesium.

A zeolite utilised in the dehydration step (I) may be used in the form of a composite with any suitable binder material. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas. Suitably, a binder material may be present in the composite in an amount of from 10 to 90 wt % based on the total weight of zeolite and binder material.

Thus, preferably, dehydration step (I) is conducted as a heterogeneous process, either in the liquid phase or in the vapour phase.

Suitably, dehydration step (I) is conducted at atmospheric or at pressures greater than atmospheric. Suitably, dehydration step (I) is conducted at temperatures of from 100° C. to 350° C. However, and, in particular where the dehydration step (I) is carried out in an adiabatic type reactor, the dehydration step (I) may be conducted over a broader temperature range, for example at temperatures in the range 100 to 450° C.

Where dehydration step (I) is carried out in the liquid phase, it is preferred to operate the process at a total reaction pressure which is sufficient to maintain product dimethyl ether in solution, such as at total reaction pressures of at least 40 bar, for example 40 to 100 barg.

Where dehydration step (I) is carried out in the vapour phase, suitable operating pressures are from atmospheric to 30 barg (atmospheric to 3000 kPa), for example 10 to 20 barg (1000 to 2000 kPa).

Preferably, liquid phase dehydration is conducted at temperatures of from 140° C. to 210° C.

Suitably, vapour phase dehydration is conducted at temperatures of from 100° C. to 450° C., preferably 150° C. to 300° C.

Suitably, dehydration step (I) is carried out in the liquid phase at a temperature of from 140° C. to 210° C. and at a total reaction pressure of 40 to 100 barg (4000 kPa to 10,000 kPa).

Suitably, dehydration step (I) is carried out in the vapour phase at a temperature of from 100° C. to 450° C., for example 150° C. to 300° C. and at a total reaction pressure of from 10 to 20 barg (1000 to 2000 kPa).

Suitably, dehydration step (I) is carried out at a gas hourly space velocity (GHSV) in the range 500 to 40,000 $h^{-1}$.

Suitably, dehydration step (I) is carried out at a liquid hourly space velocity (LHSV) is in the range 0.2 to 20 $h^{-1}$.

In one or more embodiments of the present invention, dehydration step (I) is carried out in the presence of at least one acid catalyst selected from gamma-aluminas and zeolites, for example zeolites of framework type FER and MFI and under operating conditions which are maintained such that the dehydration is conducted in the vapour phase, for example at a temperature of from 100° C. to 450° C., preferably from 150° C. to 300° C. and at a total reaction pressure of from atmospheric to 30 barg (atmospheric to 3000 kPa).

Dehydration of a methanol feed comprising predominantly methanol and small amounts of methyl formate forms a dehydration product comprising dimethyl ether, water, methanol, formic acid and a reduced amount of methyl formate. The amount of methyl formate in the dehydration product is reduced as compared to the amount of methyl formate present in the methanol feed owing to the hydrolysis of methyl formate in-situ to generate formic acid.

The dehydration product may comprise about 45 mol % or less, for example 20 to 45 mol % dimethyl ether, about 60 mol % or less, for example 20 to 45 mol % water, about 10 to 60 mol % methanol, less than 1 mol % methyl formate and less than 1 mol % formic acid, for example 0.1 mol % to 1 mol %.

Separation of formic acid from the dehydration product can in principle be achieved by any conceivable method however preference is given to distillation methods, particularly fractional distillation methods.

Suitably, in separation step (II), a distillation method is utilised in which one or more distillation columns are employed. Preferably, the distillation is conducted utilising a single distillation column. Suitably, a single column may have at least 5, such as at least 10 theoretical stages, such as at least 15 theoretical stages. Since distillation zones may have differing efficiencies 15 theoretical stages may be equivalent to at least 25 actual stages with an efficiency of about 0.7 or at least 30 actual stages with an efficiency of about 0.5.

Suitably, a distillation column for use in step (II) is operated at elevated pressure, such as at a pressure of about 0.5 barg (50 kPa) or more, such as about 5 barg to about 30 barg (500 to 3000 kPa), for example about 5 to 20 barg (500 to 2000 kPa).

At operating pressures of about 5 barg to 30 barg (500 to 3000 kPa), the heads temperature is maintained at temperatures of 120 to 180° C.

Suitably, a distillation column may be a tray or packed column.

In one or more embodiments of the present invention a distillation column for use in step (II) has at least 10 theoretical stages, such as at least 15 theoretical stages, for example 15 theoretical stages. Preferably in these embodiments the column is operated at a pressure of from 5 to 30 barg (500 to 3000 kPa) and at a heads temperature of from 120 to 180° C., for example at a pressure of 5 to 20 barg (500 to 2000 kPa) and at a heads temperature of from 120 to 165° C.

In step (II) distillation of the dehydration product of step (I) comprising dimethyl ether, water, methanol, formic acid and methyl formate generates, as a heads stream from the distillation column, a mixture comprising dimethyl ether, methanol and methyl formate which mixture may also comprise a reduced amount of formic acid compared to the amount of formic acid present in the feed to the column. Distillation is effective to achieve formic acid contents of 0.1 mol % or less in the heads mixture from dehydration feeds having formic acid contents of 0.1 mol % or more, for example 0.2 mol % or more. Desirably, water is removed from the column as the principle component of a base stream withdrawn from the distillation column. Desirably, the base stream further comprises the majority of formic acid present in the feed to the column.

Suitably, in step (II) the mixture comprising dimethyl ether, methanol, water and methyl formate is withdrawn from a distillation column as a vapour. The exact composition of this mixture will vary depending on the composition of the feed and the desired amount of water to be removed in the base stream from the column. The more water removed from the column, the richer the mixture will become in dimethyl ether and methanol. In general, however, distillation of the dehydration product obtained in step (I) results in a mixture which comprises mainly dimethyl ether together with lesser amounts of methanol, water and methyl formate. This mixture may also comprise very small amounts of formic acid, for example >0 to 0.1 mol % formic acid. Desirably, the mixture comprises >0 to 60 mol %, such as 10 to 40 mol % methanol, >0 to 60 mol %, for example 5 to 40 mol % water and dimethyl ether, for example 40 to 90 mol % dimethyl ether.

A mixture obtained in step (II) containing dimethyl ether, methanol and water may comprise methyl formate and formic acid in a combined amount of >0 to 0.5 mol %, for example >0 to 0.25 mol %.

In step (a) of the present invention, a feed mixture of dimethyl ether, methanol, water and methyl formate, such as that from obtained from step (II), is purified to remove methyl formate by a fractional distillation method in a distillation column. Methyl formate is removed as a volatile component as a sidedraw above the feed point of the feed mixture to the column, dimethyl ether is removed as a light component from the head of the column and methanol is removed as a heavy component from the base of the column.

In a typical configuration, the distillation column has at least 5, such as at least 15 theoretical stages, for example 20 to 60 theoretical stages. Since distillation columns may have differing efficiencies 15 theoretical stages may be equivalent to at least 25 actual stages with an efficiency of about 0.7 or at least 30 actual stages with an efficiency of about 0.5.

Suitably, the distillation column for use in step (a) is operated at elevated pressure, such as at a pressure of about 0.5 barg (50 kPa) or more, such as about 0.5 barg to 30 barg (50 to 3000 kPa), for example about 10 to 30 barg (1000 to 3000 kPa).

In one or more embodiments the distillation column is operated at a pressure of from 10 to 30 barg (1000 to 3000 kPa) and at a heads temperature of 40 to 90° C.

The column may be operated with a return of liquid reflux to the head of the column at a reflux to heads ratio dependent upon such factors as the required overhead stream composition. At operating pressures of from 10 to 30 barg (1000 to 3000 kPa) and at a heads temperature of 40 to 90° C. a suitable reflux ratio is in the range 1 to 5, for example 1.5 to 2.5.

The feed mixture of dimethyl ether, methanol, water and methyl formate may be fed to the column as a liquid and/or as a vapour.

The feed mixture may have a methyl formate content of >0 to 0.5 mol % or more, for example 0.01 mol % or more, such as 0.05 mol % or more, for instance 0.01 to 0.5 mol %.

In step (a) one or more additional feeds comprising dimethyl ether and methyl formate may be introduced into the distillation column. Such feeds may be dimethyl ether streams recovered as product streams from processes for the co-production of acetic acid and dimethyl ether by the hydrolysis of methyl acetate and dehydration of methanol, suitably carried out in the presence of at least one solid acid catalyst. In such cases, a dimethyl ether feed to the distillation column may comprise >0 to 0.1 mol %, such as up to 0.05 mol % or more methyl formate.

In step (a) the feed mixture comprising dimethyl ether, methanol, water and methyl formate is fed to the column at a point below the point at which the sidedraw stream is withdrawn from the column.

A sidedraw stream enriched in methyl formate is withdrawn from the column at a point above the feed point of the feed mixture to the column. Recovery of methyl formate in the sidedraw stream can be enhanced by providing sufficient stripping capacity in the distillation column below the feed point of the feed mixture to the column. Thus, it is preferred that the distillation column has at least 3 theoretical stages, for example 3 to 33 stages, such as 3 to 10 theoretical stages, below the feed point of the feed mixture comprising dimethyl ether, methanol, water and methyl formate into the column.

To optimise recovery of methyl formate in the sidedraw stream, it is preferred that the sidedraw stream is withdrawn from the column at or near the point of maximum concentration of methyl formate within the column. As would be recognised by the skilled person in the art, the point in the column at which the concentration of methyl formate will be at its highest is dependent upon the specific operating conditions employed and, in particular the specific pressure, temperature and reflux ratio employed. Concentrations of components within the column can be readily determined, for example by compositional analysis of distillation mixtures at varying stages from the column, such as compositional analysis by gas chromatographic techniques.

Typically, however, for a 40 stage column, the feed point of the feed mixture of methanol, dimethyl ether, water and methyl formate to the column may be at stages 10 to 25 counted from the head of the column and the sidedraw stream withdrawn at stages 4 to 15 counted from the head.

In one or more embodiments, the distillation column is a 40 stage column operated at a pressure of 10 to 30 burg, a heads temperature of 40 to 90° C. and a reflux ratio of from 1 to 4, the feed point of the feed mixture of methanol, dimethyl ether, water and methyl formate to the column may be at stages 10 to 25 counted from the head of the column and the sidedraw stream withdrawn at stages 4 to 15 counted from the head.

Preferably, the sidedraw stream is withdrawn from the column as a liquid. In addition to methyl formate, the sidedraw stream may comprise amounts of one or more of dimethyl ether, methanol and water.

In step (a) a heads stream depleted in methyl formate and comprising mainly dimethyl ether is withdrawn from the column, preferably as a vapour. However, alternatively and/or additionally, a heads stream comprising dimethyl ether may be withdrawn from the column as a liquid. Suitably, a heads stream comprises at least 60 mol % dimethyl ether, for example 60 to >95 mol % dimethyl ether. Suitably, a heads stream is condensed and a portion of the condensed liquid is returned to the column as reflux.

The base stream depleted in methyl formate as compared to the feed mixture comprises methanol and water and preferably comprises the majority of methanol and water present in the feed mixture to the column. The base stream may also comprise a small proportion of the methyl formate present in the feed mixture.

In various embodiments of step (a) of the present invention, the process is effective to provide methyl formate contents in the base stream of 0 to 0.2 mol %, or 0 to 0.05 mol % where the feed mixture has a methyl formate content of more than 0.05 mol %, such as 0.2 mol % or more.

In one or more embodiments of step (a), a feed mixture of dimethyl ether, methanol, water and methyl formate might comprise >0 to 60 mol %, for example 10 to 40 mol % methanol, >0 to 60 mol %, for example 5 to 40 mol % water, and the balance dimethyl ether, for example 40 to 90 mol % dimethyl ether and methyl formate, for example more than 0.01 mol % or more than 0.05 mol %, for example 0.01 to 0.5 mol % methyl formate. In such cases, the present invention is effective to provide a base stream having a methyl formate content of 0 to 0.05 mol %.

Advantageously, the base stream or a part thereof depleted in methyl formate and comprising methanol and water from the distillation of step (a) can be utilised directly in a process for the co-production of acetic acid and dimethyl ether by the dehydration of methanol and hydrolysis of methyl acetate in the presence of a solid acid catalyst without the need for further purification.

Methyl acetate may be produced by carbonylating alkylethers, for example dimethyl ether with carbon monoxidecontaining feeds in the presence of zeolite catalysts. Such carbonylation processes are described in, for example U.S. Pat. No. 7,465,822. It has been found in accordance with the present invention that such product methyl acetate can contain quantities of acetaldehyde. It has also been found in accordance with the present invention that the presence of acetaldehyde can have a detrimental effect on the catalytic performance of solid acid catalysts and, in particular zeolite catalysts, utilised in processes for the co-production of acetic acid and dimethyl ether.

Advantageously, it has now been found that in step (a) distillation of mixtures of dimethyl ether, methanol, water, methyl formate together with methyl acetate and acetaldehyde, the acetaldehyde and typically the majority of the acetaldehyde, can be removed together with methyl formate as a component of the sidedraw stream from the column.

Thus, in one or more embodiments of the present invention, in step (a) the feed mixture of dimethyl ether, water, methanol and comprising methyl formate in an amount for example up to 0.5 mol %, such as 0.01 mol % to 0.2 mol % is distilled in the distillation column together with a mixture comprising methyl acetate and acetaldehyde, suitably comprising up to 1 mol %, for example >100 ppm to 1 mol % acetaldehyde.

Thus, in one or more embodiments of the present invention, a feed mixture of mainly methyl acetate and acetaldehyde in which the acetaldehyde content is >0 to 1 mol %, is fed to the distillation column. A methyl acetate and acetaldehyde feed mixture may contain 100 ppm or more or 500 ppm or more or 1000 ppm or more or 2000 ppm or more or up to 1 mol % acetaldehyde.

A feed mixture of methyl acetate and acetaldehyde may be derived from the production of methyl acetate by the carbonylation of dimethyl ether with a carbon monoxide in the presence of a zeolite carbonylation catalyst and optionally hydrogen. In such cases the feed mixture to the distillation column might have an acetaldehyde content of >100 ppm up to 1 mol %, such as 100 ppm or more, or 200 ppm or more, or 500 ppm or more or 1000 ppm or more, or 2000 ppm or more or up to 1 mol % acetaldehyde. The feed mixture may further comprise some dimethyl ether and small amounts of acetic acid and dissolved gases such as one or more of carbon oxides and hydrogen.

Desirably, a feed mixture of methyl acetate and acetaldehyde is fed to the column at a point below the point at which the sidedraw stream is withdrawn from the column. Typically, for a 40 stage column the feed point of the feed mixture of methyl acetate and acetaldehyde to the column may be at stages 10 to 25 counted from the head of the column and the sidedraw stream withdrawn at stages 4 to 15 counted from the head.

The feed mixture of methyl acetate and acetaldehyde may be fed as an additional feed to the column. Alternatively and/or additionally, the feed mixture of methyl acetate and acetaldehyde may be combined with the feed mixture of methanol, dimethyl ether, water and methyl formate. The feed mixture of methyl acetate and acetaldehyde may be fed to the column as a liquid or as a vapour, preferably as a liquid.

Advantageously, in step (a) acetaldehyde may be removed as a volatile component of the sidedraw stream from the column.

In one or more embodiments, a methyl acetate feed to the column comprises >100 ppm to 1 wt % acetaldehyde and acetaldehyde is removed as a component of the sidedraw stream from the column and the base stream comprises less than 100 ppm wt acetaldehyde.

Methyl acetate, as a heavy component of the distillation mixture, is removed from the column together with methanol as part of the base stream. Thus, the base stream comprising methanol and water may further comprise methyl acetate and an acetaldehyde content of not more than 100 ppm.

The present invention is effective to purify a feed mixture of methyl acetate and acetaldehyde supplied to the column in step (a) such that the base stream from the distillation column has an acetaldehyde content of 100 ppm or less or 50 ppm or less where the feed mixture supplied has an acetaldehyde content of more than 100 ppm up to 1 wt %.

In one or more embodiments, the base stream from the distillation column in step (a) has an acetaldehyde content of 100 ppm or less or less than 50 ppm where the feed mixture of methyl acetate and acetaldehyde has an acetaldehyde content of more than 100 ppm, more than 250 ppm or more than 500 ppm up to 1 wt % and a methyl formate content of 0.05 mol % or less, or 0.01 mol % or less where the feed mixture of methanol, dimethyl ether, water and methyl formate has a methyl formate content of more than 0.05 mol % up to 0.1 mol %.

Advantageously, embodiments of the present invention provide a means of simultaneously reducing undesirable methyl formate and acetaldehyde compounds from feedstocks to acetic acid and dimethyl ether co-production processes to acceptable levels for use therein. In this manner, the amount of formic acid in the co-production process is controlled and the deleterious effect of acetaldehyde on the catalytic performance of catalysts, particularly solid acid catalysts such as Brønsted acid catalysts employed in the co-production process is eliminated or at least mitigated.

In preferred embodiments of the present invention an additional feed of methyl acetate and acetaldehyde is fed to the distillation column and the base stream further comprises methyl acetate and an acetaldehyde content of not more than 100 ppm. Desirably, the base stream has a methyl formate content of 0.05 mol % or less, preferably 0.01 mol % or less.

In step (b) of the present invention the base stream from the distillation column or at least a part thereof comprising methanol and water is contacted together with a source of methyl acetate in the presence of at least one solid acid catalyst to generate a crude reaction product comprising acetic acid and dimethyl ether.

If methyl acetate-containing streams are distilled with the dimethyl ether/methanol/water/methyl formate feed mixture in step (a), methyl acetate is likely to be present as a component of the base stream and the combined base stream or part thereof comprising methanol, water and methyl acetate is fed to the dehydration-hydrolysis reaction. Alternatively and/or additionally methyl acetate may be supplied as one or more separate feeds to the dehydration-hydrolysis reaction.

Depending on the exact composition of the base stream to the dehydration-hydrolysis reaction, it may be desirable to supply additional methanol, methyl acetate and/or water to the reaction.

The hydrolysis of methyl acetate to produce acetic acid and dehydration of methanol to produce dimethyl ether can be represented by equations (1) and (2) respectively:

$$CH_3COOCH_3 + H_2O \rightleftharpoons CH_3COOH + CH_3OH \quad (1)$$

$$2CH_3OH \rightleftharpoons CH_3OCH_3 + H_2O \quad (2)$$

The molar ratio of methanol to methyl acetate useful for the dehydration-hydrolysis reaction may be any desired ratio, but suitably the molar ratio of methanol:methyl acetate is in the range 1:0.1 to 1:20.

One or more catalysts may be utilised in the dehydration-hydrolysis reaction. Any suitable catalyst or catalysts may be used provided that it/they are effective to catalyse the hydrolysis of methyl acetate to produce acetic acid and are also effective to catalyse the dehydration of methanol to form dimethyl ether. One or more catalysts may be employed which are effective to catalyse both the hydrolysis and dehydration reactions.

Alternatively, one or more catalysts effective for catalysing the hydrolysis may be used in addition to or as an admixture with one or more catalysts for the dehydration reaction. Where it is desired to employ two or more different catalysts, such catalysts may be utilised in the form of alternating catalyst beds or as one or more intimately mixed catalyst beds.

Preferably, one or more solid acid catalysts are utilised for the dehydration-hydrolysis reaction, such as one or more solid Brønsted acid catalysts. Solid acid catalysts useful for the dehydration of methanol include one or more of the catalysts as described above in respect of dehydration step (I) of the present invention.

Zeolites known to be effective for the hydrolysis of methyl acetate to produce acetic acid include zeolite Y, zeolite A, zeolite X and mordenite. If desired, these zeolites can be usefully employed as a catalyst in the dehydration-hydrolysis reaction of the present invention.

Particularly useful zeolite catalysts for use in the dehydration-hydrolysis reaction include zeolites having a 2-dimensional or 3 dimensional channel system and at least one channel of which has a 10-membered ring. Specific non-limiting examples of such zeolites include zeolites of framework type FER (typified by ferrierite and ZSM-35), MFI (typified by ZSM-5), MFS (typified by ZSM-57), HEU (for example clinoptilolite) and NES (typified by NU-87).

In step (b) a zeolite catalyst may be employed in an exchanged form. Exchanged forms of zeolites can be prepared by techniques such as ion-exchange and impregnation. These techniques are well-known in the art and typically involve the exchange of the hydrogen or ammonium cations of a zeolite with metal cations. For example, in the present invention, the zeolite may be in an exchanged form with one or more alkali metal cations for example sodium, lithium, potassium and cesium. Suitable exchanged form zeolites include ferrierite and ZSM-35 exchanged with one or more of sodium, lithium, potassium and cesium.

A zeolite may be used in the form of a composite with any suitable binder material. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas. Suitably, a binder material may be present in the composite in an amount of from 10 to 90 wt % based on the total weight of zeolite and binder material.

The dehydration-hydrolysis reaction may be carried out as a heterogeneous vapour phase process or as a liquid phase process. If it is desired to conduct the reaction as a vapour phase process, it is preferable to volatilise liquid feed(s), for example in a pre-heater prior to contact with the catalyst.

The dehydration-hydrolysis reaction may be carried out at temperatures of about 100° C. to 350° C. and at atmospheric pressure or pressures greater than atmospheric.

In one or more embodiments of the present invention, the dehydration-hydrolysis reaction is conducted as a vapour phase process at a temperature of about 150° C. to 350° C. and a pressure of atmospheric to 30 barg (atmospheric to 3000 kPa), for example 5 to 20 barg (500 kPa to 2000 kPa). Suitably, in such cases, the dehydration-hydrolysis reaction is carried out at a gas hourly space velocity (GHSV) in the range 500 to 40,000 $h^{-1}$.

In one or more embodiments of the present invention, the dehydration-hydrolysis reaction is conducted as a liquid phase process at a temperature of from about 140° C. to about 210° C. and at a pressure which is sufficient to maintain dimethyl ether product in solution, such as pressures of 40 barg (4000 kPa) or higher, for example 40 to 100 barg (4000 to 10,000 kPa). Suitably, in such cases, the dehydration-hydrolysis reaction is carried out at a liquid hourly space velocity (LHSV) in the range 0.2 to 20 $h^{-1}$.

The dehydration-hydrolysis reaction may be carried out using any suitable technique and apparatus, for example by reactive distillation. Reactive distillation techniques and apparatus therefor are well-known. The base stream or at least part thereof comprising methanol and water and optionally together with methyl acetate, can be supplied to a conventional reactive distillation column, operated at, for example a pressure in the range atmospheric to 20 barg (atmospheric to 2000 kPa) and at a reaction temperature of about 100° C. to 250° C., to produce a crude reaction product comprising a mixture of acetic acid and dimethyl ether, which mixture is inherently separated within the reactive distillation column to recover therefrom a product stream rich in dimethyl ether, typically recovered as a heads stream from the column, and a product stream rich in acetic acid, typically recovered as a base stream from the column.

Alternatively, the dehydration-hydrolysis reaction may be carried out in a fixed bed reactor or a slurry bed reactor. Dimethyl ether has a low boiling point (−24° C.) and acetic acid has a high boiling point (118° C.). Thus, acetic acid and dimethyl ether may be recovered from the dehydration-hydrolysis reaction product by conventional purification methods, such as by distillation in one or more conventional distillation columns. Suitable distillation columns include tray or packed columns. The temperatures and pressures employed in the columns can vary. Suitably, a distillation column may be operated at a pressure, for example of atmospheric to 20 barg (0 to 2000 kPa). Typically, a stream rich in dimethyl ether is recovered as a heads stream from the distillation column, and a stream rich in acetic acid is recovered as a base stream from the column.

The process of the present invention is effective to recover acetic acid having a formic acid content of 500 ppm or less or 100 ppm or less or 50 ppm or less and, in particular where the base stream to the dehydration-hydrolysis reaction has a methyl formate content of 0.001 mol % or more, for example 0.01 mol % or more.

Recovered acetic acid may be sold or may be used as a feedstock in a variety of chemical processes, such as the manufacture of vinyl acetate or ethyl acetate.

Recovered dimethyl ether may be sold or used as a fuel or as a feedstock to carbonylation or other chemical processes.

The base stream recovered in step (a) from the distillation of the methanol/dimethyl ether/water/methyl formate feed mixture comprises methanol and water and a reduced amount of methyl formate as compared to the feed mixture. Methyl formate, formic acid, methanol and water exist in equilibrium, that is to say methyl formate hydrolyses in hydrous environments to generate formic acid and formic acid in the presence of methanol is esterified (with methanol) to generate methyl formate and water. As a consequence, by removing in step (a) the majority of the methyl formate from the feed mixture to the distillation column as a component of the sidedraw stream withdrawn from the column the concentration of formic acid is caused to be in excess of the equilibrium concentration. In the dehydration-hydrolysis process, this excess formic acid is re-esterified to form methyl formate which is easily removed as a light component together with produced dimethyl ether. Thus, typically dimethyl ether streams recovered from the dehydration-hydrolysis reaction comprise small amounts of methyl formate.

Thus, in preferred embodiments of the present invention, wherein in step (c) dimethyl ether recovered from the crude reaction product comprises methyl formate, at least part of the recovered dimethyl ether is returned as a feed to the distillation column in step (a) to remove methyl formate therefrom as a component of the sidedraw stream from the column.

Advantageously, by recycling dimethyl ether streams in this manner the amount of formic acid present in product acetic acid from the co-production process can be controlled to acceptable levels such that the need for complex equipment and processes to separate formic acid from acetic acid is unnecessary.

The process of the present invention may be operated as a continuous process or as a batch process, but is preferably operated as a continuous process.

The sidedraw stream withdrawn from the distillation column enriched in methyl formate typically comprises one or more feed components to the distillation column. Thus, the sidedraw stream may further comprise one or more of dimethyl ether, water and methanol. If a mixture of methyl acetate and acetaldehyde is also fed to the distillation column in step (a), the majority of the acetaldehyde may be withdrawn as a component of the sidedraw stream. Methyl acetate may also be a component of the sidedraw stream.

Dimethyl ether, methanol and methyl acetate are valuable as feedstock components to the process of the present invention and to other chemical processes. It is therefore desirable to recover these components from mixtures thereof and to further eliminate acetaldehyde and methyl formate components from the process. Thus, the present invention may further comprise step ($a^1$) in which at least a portion of the sidedraw stream withdrawn from the distillation column in step (a) and comprising methyl formate, dimethyl ether and one or more of methanol and water is supplied as feed to a further distillation column and distilled therein to withdraw from the distillation column a sidedraw stream enriched in methyl formate as compared to the feed mixture, a heads stream comprising dimethyl ether and a base stream comprising one or more of methanol and water.

In step (a¹), methyl formate is removed as a volatile component as a sidedraw stream from the distillation column dimethyl ether is removed as a light component from the head of the column and methanol and water are removed as heavy components from the base of the column.

In a preferred embodiment, in step (a¹), the sidedraw feed to the distillation column further comprises methyl acetate and acetaldehyde. In this embodiment, acetaldehyde is removed as a component of the sidedraw stream from the distillation column and methyl acetate is removed from the column as a component of the base stream.

In preferred embodiments of step (a¹) the sidedraw stream comprises the majority of methyl formate present in the feed to the column and more preferably, if present in the feed to the column, the majority of the acetaldehyde. Desirably, 80% or more, such as 85% or more methyl formate and, if present, 90% or more, such as 95% or more acetaldehyde are removed as components of the sidedraw stream.

A typical configuration of the distillation column in step (a¹) has up to 40 theoretical stages. Suitably, the distillation column may have 20 to 35 theoretical separation stages and the feed to the column may be introduced at stages 5 to 25 counted from the head of the column and a sidedraw stream withdrawn from the column at stages 5 to 25 counted from the head.

In step (a¹) it not necessary to withdraw the sidedraw from above the feed point to the column, the sidedraw stream may be withdrawn from the column at any desired point but it is desirable that the sidedraw stream is withdrawn from the column at or near the point of maximum concentration of methyl formate or if present, acetaldehyde within the column. In this manner the majority of the methyl formate and acetaldehyde fed to the column and at the greatest concentration thereof can be removed from the column.

Preferably, in step (a¹) the sidedraw stream is withdrawn from the distillation column as a vapour.

If desired, the sidedraw stream withdrawn from the distillation column in step (a¹) may be discarded from the process, for example by burning.

In one or more embodiments, the feed to the distillation column in step (a¹) may comprise 0 to 30 mol %, for example 5 to 20 mol %, methanol, 0 to 30 mol %, for example 5 to 20 mol % water, 0 to 30 mol %, for example 5 to 20 mol % methyl acetate, 0 to 1 mol % or more, such as 1 to 2 mol % methyl formate and 2 mol % or more, such as 2 to 3 mol % acetaldehyde and the balance dimethyl ether. In such cases, distillation is effective to provide a sidedraw stream comprising methyl formate and acetaldehyde in a total concentration of 20 to 40 mol % and which sidedraw stream contains at least 85%, for example at least 90% of the combined amount of methyl formate and acetaldehyde present in the feed to the column.

Suitably, in step (a¹) the distillation column is operated at elevated pressure, such as at a pressure of about 0.5 barg (50 kPa) or more, such as about 0.5 barg to 30 barg (50 to 3000 kPa), for example about 10 to 30 barg (1000 to 3000 kPa).

To reduce equipment complexity and cost of the process, it is desirable to operate the distillation column in step (a¹) at a slightly lower pressure or at the same pressure as the pressure of the distillation column in step (a). Desirably, the distillation column in step (a¹) is operated at 0.1 to 1 barg lower pressure than the distillation column of step (a).

In one or more embodiments, the distillation column in step (a¹) is operated at a pressure of from 10 to 30 barg (1000 to 3000 kPa) and at a heads temperature of about 40 to 90° C.

Preferably, the feed to the distillation column in step (a¹), that is the sidedraw removed from the distillation column in step (a), is fed to the column as a liquid.

Typically, as a light component, the majority of the dimethyl ether present in the feed to the distillation column in step (a¹) is removed as a heads stream from the distillation column. The heads stream may be removed as a liquid or vapour, preferably as a liquid.

Conveniently, dimethyl ether withdrawn as a heads stream from the distillation column of step (a¹) may be condensed and may be fed as a liquid return stream or as part of a return stream to the distillation column in step (a), suitably at or below the feed point to the column of the feed mixture to the column, and preferably below the point at which the sidedraw stream is withdrawn from the column.

Suitably, the distillation column in step (a¹) may be operated at a reflux ratio of 1 to 4 and a boil-up ratio of 2 to 15.

Typically, as a heavy component, the majority of methyl acetate, and if present in the feed to the column methanol and water are removed as components of the base stream from the column. Typically, the base stream is removed as a liquid.

Conveniently, in step (a¹) the base stream or a portion thereof from the distillation column comprising one or more of methyl acetate, methanol and water and may be fed as a liquid return stream or as part of a return stream to the distillation column in step (a), suitably at or below the feed point to the column of the feed mixture, and preferably below the point at which the sidedraw stream is withdrawn from the column.

Suitably, at least a portion of the base stream and at least a portion of liquid dimethyl ether may be fed as a single combined return stream to the distillation column in step (a).

Thus, in preferred embodiments of the present invention, one or more of dimethyl ether, methanol, water and methyl acetate withdrawn from the distillation column in step (a¹) are returned to the distillation column in step (a).

The invention is now illustrated with reference to the following non-limiting Examples.

Example 1

This Example demonstrates a process for the co-production of acetic acid and dimethyl ether in which the purity of acetic acid, and in particular the formic acid content of produced acetic acid, is controlled in accordance with the present invention. Reference is made to FIG. 1 and Table 1. FIG. 1 illustrates schematically an integrated unit (110) for carrying out embodiments of the process of the present invention. A methanol stream (6) comprising methanol, water and dimethyl ether is introduced, preferably as a vapour stream and a GHSV of 500 to 40,000 h$^{-1}$ into reactor (111) containing a dehydration catalyst, suitably a solid acid catalyst, suitably a zeolite catalyst. Suitably, the reactor (111) is maintained under conditions of 100 to 350° C., preferably 150 to 300° C. and a pressure of 10 to 20 barg. In reactor (111), dehydration of the methanol takes place to produce a crude dehydration product (10) comprising dimethyl ether, water and unreacted methanol which is withdrawn from reactor (111), passed to a heat exchanger (112) to cool the crude dehydration product and the cooled dehydration product stream (7) is introduced into distillation column (113) equipped with a reboiler. Distillation column (113) has 15 theoretical stages with feed of the crude dehydration product to stage 10 (counted from the head of the column) and is operated at 13.5 barg and a heads temperature of 152° C. a base temperature of 198° C., a reflux ratio of 0.35 and a boil-up ratio of 1.0. A stream (9) comprising water and formic acid is removed as a base stream from the column (113). A stream (8) comprising dimethyl ether, methanol, water and methyl formate is removed from the column (113) as a heads stream. The dimethyl ether stream (8) is passed to distillation column (114) equipped with a reboiler. Distillation column (114) has 20 theoretical stages with the dimethyl ether feed point at stage 15 (counted from the head of the column) and is operated at 11.7 barg, a heads temperature of 48° C., a base temperature of 156° C., a reflux ratio of 2.5 and a boil-up ratio of 0.082. Dimethyl ether is withdrawn from the distillation column (114) as heads stream (12). A vent stream (11) comprising mainly carbon oxides and hydrogen is also withdrawn from the column (114). A sidedraw stream (14) comprising the majority of the methyl formate present in the feed to the column is removed from the column at stage 7 (counted from the head of the column). A stream (13) comprising methanol and water is withdrawn as a base stream from the column. Stream (13) and a methyl acetate stream (17) comprising mainly methyl acetate are mixed in mixer (115), for example a T-piece and the mixed stream (15) is supplied to dehydration-hydrolysis reactor (116), such as a fixed bed reactor wherein it is contacted with at least one solid acid catalyst, for example a heteropolyacid or zeolite catalyst at elevated pressure and a temperature of 100 to 350° C. to generate a reaction product comprising acetic acid and dimethyl ether, withdrawn from reactor (116) as product stream (16).

Utilising the procedure and apparatus of the type illustrated in FIG. 1, simulations were carried out using ASPEN software version 7.3. The compositions of the streams in this Example (in units kmol/hr and mol %) are shown in Table 1 in which the following abbreviations are used:

CO—carbon monoxide
$CO_2$—carbon dioxide
$H_2$—hydrogen
MeOH—methanol
AcOH—acetic acid
DME—dimethyl ether
MeOAc—methyl acetate
MeOFO—methyl formate
FOOH—formic acid As can be seen from Table 1 operation of a process in accordance with embodiments of the present invention allows the efficient removal of formic acid and methyl formate to provide an acceptable level of formic acid in an acetic acid product.

TABLE 1

| mol flow | 6 | mol % | 7 | mol % | 8 | mol % | 9 | mol % | 12 | mol % |
|---|---|---|---|---|---|---|---|---|---|---|
| CO | 1.0 | 0.1 | 1.0 | 0.1 | 1.0 | 0.1 | 0.0 | 0.0 | 0.1 | 0.0 |
| $CO_2$ | 6.0 | 0.6 | 6.0 | 0.6 | 6.0 | 0.7 | 0.0 | 0.0 | 4.2 | 1.1 |
| $H_2$ | 2.0 | 0.2 | 2.0 | 0.2 | 2.0 | 0.2 | 0.0 | 0.0 | 0.2 | 0.0 |
| MeOH | 843.0 | 84.3 | 122.0 | 12.2 | 122.0 | 14.4 | 0.0 | 0.0 | 0.4 | 0.1 |
| AcOH | 0.0 | 0.0 | 0.0 | 0.0 | 0.0 | 0.0 | 0.0 | 0.0 | 0.0 | 0.0 |
| Water | 79.0 | 7.9 | 438.8 | 43.9 | 289.8 | 34.1 | 149.0 | 99.3 | 0.0 | 0.0 |
| DME | 66.0 | 6.6 | 427.2 | 42.7 | 427.2 | 50.3 | 0.0 | 0.0 | 385.1 | 98.7 |
| MEOAc | 0.0 | 0.0 | 0.0 | 0.0 | 0.0 | 0.0 | 0.0 | 0.0 | 0.0 | 0.0 |
| MEOFO | 3.000 | 0.300 | 1.557 | 0.156 | 1.557 | 0.183 | 0.000 | 0.0 | 0.180 | 0.046 |
| FOOH | 0.0 | 0.0 | 1.4 | 0.144 | 0.5 | 0.055 | 1.0 | 0.649 | 0.0 | 0.0 |

| mol flow | 13 | mol % | 14 | mol % | 16 | mol % | 17 | mol % |
|---|---|---|---|---|---|---|---|---|
| CO | 0.0 | 0.0 | 0.0 | 0.0 | 0.0 | 0.0 | 0.0 | 0.0 |
| $CO_2$ | 0.0 | 0.0 | 0.0 | 0.0 | 0.0 | 0.0 | 0.0 | 0.0 |
| $H_2$ | 0.0 | 0.0 | 0.0 | 0.0 | 0.0 | 0.0 | 0.0 | 0.0 |
| MeOH | 112.0 | 27.6 | 9.6 | 47.8 | 48.8 | 3.5 | 0.0 | 0.0 |
| AcOH | 0.0 | 0.0 | 0.0 | 0.0 | 186.0 | 13.2 | 0.0 | 0.0 |
| Water | 289.5 | 71.3 | 0.2 | 1.2 | 228.2 | 16.2 | 0.0 | 0.0 |
| DME | 4.1 | 1.0 | 8.8 | 44.0 | 128.6 | 9.1 | 0.0 | 0.0 |
| MEOAc | 0.0 | 0.0 | 0.0 | 0.0 | 814.0 | 57.9 | 1000.0 | 100.0 |
| MEOFO | 0.005 | 0.0012 | 1.369 | 6.845 | 0.229 | 0.016 | 0.000 | 0.0 |
| FOOH | 0.0 | 0.0 | 1.443 | 0.144 | 0.470 | 0.055 | 0.973 | 0.649 |

Example 2

Figure 2:
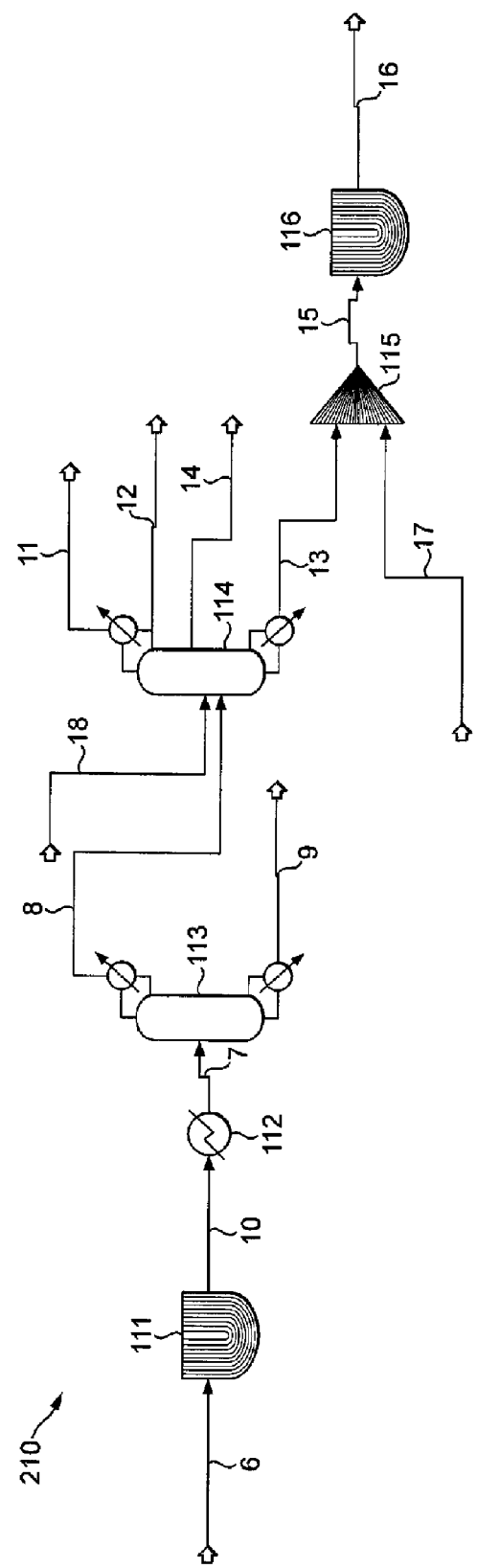
FIG. 2 is a schematic diagram illustrating an embodiment of the present invention for the co-production of acetic acid and dimethyl ether in which methyl formate and acetaldehyde are removed therefrom.

Example 1 was repeated with the addition onto stage 14 (counted from the head) of distillation column (114) of a feed stream (18) comprising methyl acetate and acetaldehyde. Distillation column (114) has 30 theoretical stages with the dimethyl ether feed point at stage 15 (counted from the head of the column) and is operated at 11.7 barg, a heads temperature of 48° C., a base temperature of 146° C., a reflux ratio of 3.8 and a boil-up ratio of 0.66. Acetaldehyde is removed from the column (114) as a component of sidedraw stream (14) withdrawn from stage 6 of the column. The flow scheme is illustrated in FIG. 2 as integrated unit (210) and the stream compositions (in kmol/hr and mol %) are provided in Table 2 below. In the Table the following abbreviations are used:

CO—carbon monoxide
$CO_2$—carbon dioxide
$H_2$—hydrogen
MeOH—methanol
AcOH—acetic acid
DME—dimethyl ether
MeOAc—methyl acetate
MeOFO—methyl formate AcH—acetaldehyde
FOOH—formic acid As can be seen from Table 2 operation of a process in accordance with embodiments of the present invention allows the efficient removal of formic acid, methyl formate and acetaldehyde to provide acceptable levels of acetaldehyde in the feed to the dehydration-hydrolysis reaction and ii) formic acid in an acetic acid product.

comprising mainly methanol with lesser amounts of water, dimethyl ether and methyl formate is removed as a base stream from the column (310). A sidedraw stream (37) comprising the majority of the methyl formate fed to the column (310) is removed from the column at stage 11.

Figure 3:
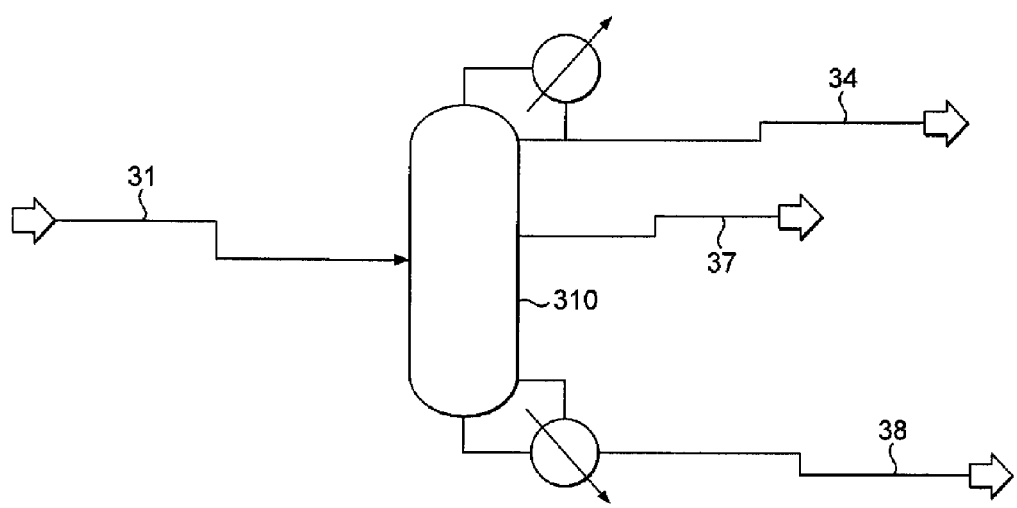
FIG. 3 is a schematic diagram illustrating an embodiment of the present invention for the purification of a feed mixture of dimethyl ether/methanol/water/methyl formate to remove methyl formate therefrom and provide a purified methanol feedstock.

Utilising the procedure and apparatus of the type illustrated in FIG. 3, simulations were carried out using ASPEN software version 7.3. The stream compositions (in kmol/hr

TABLE 2

| mol flow | 6 | | 7 | | 8 | | 9 | | 12 | |
|---|---|---|---|---|---|---|---|---|---|---|
| | | | | | mol % | | | | | |
| CO | 1.0 | 0.1 | 1.0 | 0.1 | 1.0 | 0.1 | 0.0 | 0.0 | 0.1 | 0.0 |
| $CO_2$ | 6.0 | 0.6 | 6.0 | 0.6 | 6.0 | 0.7 | 0.0 | 0.0 | 4.2 | 1.1 |
| $H_2$ | 2.0 | 0.2 | 2.0 | 0.2 | 2.0 | 0.2 | 0.0 | 0.0 | 0.2 | 0.1 |
| MeOH | 843.0 | 84.3 | 122.0 | 12.2 | 122.0 | 14.4 | 0.0 | 0.0 | 0.1 | 0.0 |
| AcOH | 0.0 | 0.0 | 0.0 | 0.0 | 0.0 | 0.0 | 0.0 | 0.0 | 0.0 | 0.0 |
| Water | 79.0 | 7.9 | 438.8 | 43.9 | 289.8 | 34.1 | 149.0 | 99.3 | 0.1 | 0.0 |
| DME | 66.0 | 6.6 | 427.2 | 42.7 | 427.2 | 50.3 | 0.0 | 0.0 | 386.7 | 98.7 |
| MeOAc | 0.0 | 0.0 | 0.0 | 0.0 | 0.0 | 0.0 | 0.0 | 0.0 | 0.0 | 0.0 |
| MeOFO | 3.0 | 0.300 | 1.557 | 0.156 | 1.557 | 0.183 | 0.000 | 0.0 | 0.191 | 0.049 |
| AcH | 0.0 | 0.0 | 0.000 | 0.0 | 0.000 | 0.0 | 0.000 | 0.0 | 0.317 | 0.081 |
| FOOH | 0.0 | 0.0 | 1.443 | 0.144 | 0.470 | 0.055 | 0.973 | 0.649 | 0.000 | 0.0 |

| mol flow | 13 | | 14 | | 16 | | 17 | | 18 | |
|---|---|---|---|---|---|---|---|---|---|---|
| | | | | | mol % | | | | | |
| CO | 0.0 | 0.0 | 0.0 | 0.0 | 0.0 | 0.0 | 0.0 | 0.0 | 0.0 | 0.0 |
| $CO_2$ | 0.0 | 0.0 | 0.0 | 0.0 | 0.0 | 0.0 | 0.0 | 0.0 | 0.0 | 0.0 |
| $H_2$ | 0.0 | 0.0 | 0.0 | 0.0 | 0.0 | 0.0 | 0.0 | 0.0 | 0.0 | 0.0 |
| MeOH | 120.9 | 13.4 | 1.0 | 5.2 | 50.6 | 2.7 | 0.0 | 0.0 | 0.0 | 0.0 |
| AcOH | 0.0 | 0.0 | 0.0 | 0.0 | 235.8 | 12.4 | 0.0 | 0.0 | 0.0 | 0.0 |
| Water | 288.3 | 31.9 | 1.4 | 6.9 | 205.5 | 10.8 | 0.0 | 0.0 | 0.0 | 0.0 |
| DME | 0.9 | 0.10 | 10.5 | 52.4 | 153.9 | 8.1 | 0.0 | 0.0 | 0.0 | 0.0 |
| MeOAc | 493.6 | 54.6 | 5.4 | 27.0 | 1257.7 | 66.0 | 1000.0 | 100.0 | 499.0 | 99.8 |
| MeOFO | 0.347 | 0.038 | 1.016 | 5.08 | 0.436 | 0.023 | 0.000 | 0.0 | 0.000 | 0.0 |
| AcH | 0.014 | 0.0016 | 0.661 | 3.31 | 0.014 | 0.001 | 0.000 | 0.0 | 1.000 | 0.200 |
| FOOH | 0.470 | 0.052 | 0.000 | 0.0 | 0.381 | 0.020 | 0.000 | 0.0 | 0.000 | 0.0 |

Example 3

This Example demonstrates a process for purifying a mixture of dimethyl ether/methanol/water/methyl formate in accordance with the present invention. Reference is made to FIG. 3 and Table 3. FIG. 3 illustrates schematically a distillation column (310) for carrying out embodiments of the process of the present invention. A feed stream (31)

and mol %) employed in this Example are shown in Table 3 below. In the Table, the following abbreviations are used:

MeOH—methanol
DME—dimethyl ether
MeOFO—methyl formate

TABLE 3

| mol flow | 31 | | 34 | | 38 | | 37 | |
|---|---|---|---|---|---|---|---|---|
| | | | | mol % | | | | |
| MeOH | 289.00 | 14.10 | 0.26 | 0.03 | 286.90 | 27.86 | 1.85 | 18.50 |
| Water | 737.00 | 35.96 | 0.003 | 0.00 | 736.80 | 71.60 | 0.22 | 2.20 |
| DME | 1022.00 | 49.89 | 1009.0 | 99.96 | 6.00 | 0.58 | 7.04 | 70.40 |
| MeOFO | 1.00 | 0.049 | 0.10 | 0.01 | 0.01 | 0.001 | 0.89 | 8.90 | comprising dimethyl ether, methanol, water and methyl formate is introduced into distillation column (310) equipped with a reboiler. Distillation column (310) has 20 theoretical stages with the feed point on stage 15 (counted from the head of the column) and is operated at a pressure of 11.7 barg, a heads temperature of 55° C. and a base temperature of 116° C. A heads stream (34) comprising mainly dimethyl ether is removed from the column (310) condensed and a portion thereof is returned to the column at a reflux ratio of 1.1 and a boil-up ratio of 0.18. A stream (38)

As can be seen from Table 3 a feed mixture comprising dimethyl ether, methanol, water and methyl formate can be purified in accordance with the invention to reduce its methyl formate content to provide a purified methanol stream suitable for use as a feedstock in processes for the co-production of acetic acid and dimethyl ether.

The invention claimed is:
1. A process for the co-production of acetic acid and dimethyl ether which process comprises:

(a) purifying a mixture of dimethyl ether, methanol, water and methyl formate by:
  (i) feeding the mixture of dimethyl ether, methanol, water and methyl formate to a distillation column;
  (ii) distilling the feed mixture of dimethyl ether, methanol, water, formic acid and methyl formate to generate a heads stream depleted in methyl formate as compared to the feed mixture, a base stream depleted in methyl formate as compared to the feed mixture and comprising methanol and water and a sidedraw stream enriched in methyl formate as compared to the feed mixture;
  (iii) withdrawing from the column the sidedraw stream enriched in methyl formate at a point above the feed point of the feed mixture to the column
(b) feeding at least part of the base stream comprising methanol and water together with methyl acetate to a dehydration-hydrolysis reaction and dehydrating methanol and hydrolysing methyl acetate therein in the presence of at least one solid acid catalyst to produce a crude reaction product comprising acetic acid and dimethyl ether;
(c) recovering acetic acid and dimethyl ether from the crude reaction product; and
wherein dimethyl ether recovered from the crude reaction product comprises methyl formate and at least part of the recovered dimethyl ether is returned as a feed to the distillation column in step (a).

2. A process according to claim 1 in which process the feed mixture to the distillation column comprising dimethyl ether, methanol, water and methyl formate is obtained by
  (I) dehydrating a methanol feed comprising predominantly methanol together with small amounts of methyl formate to form a dehydration product comprising dimethyl ether, water, methanol, formic acid and a reduced amount of methyl formate;
  (II) separating formic acid from the dehydration product to form a mixture comprising dimethyl ether, methanol, water and methyl formate.

3. A process according to claim 1 wherein in step (a) the sidedraw stream enriched in methyl formate is withdrawn from the column as a liquid.

4. A process according to claim 1 wherein in step (a) the sidedraw stream enriched in methyl formate is withdrawn from the distillation column at or near the point of maximum concentration of methyl formate within the column.

5. A process according to claim 1 wherein in step (a) the distillation column has at least 3 theoretical stages below the feed point of the feed mixture to the column.

6. A process according to claim 1 wherein in step (a) the feed mixture has a methyl formate content of >0 to 0.5 mol %.

7. A process according to claim 1 wherein in step (a) the distillation column is operated at a pressure of from 10 to 30 barg, a heads temperature of 40 to 90° C. and at a reflux ratio in the range 1 to 5.

8. A process according to claim 1 wherein in step (a) the methyl formate content of the base stream is 0.05 mol % or less.

9. A process according to claim 1 wherein in step (b) methyl acetate is present as a component of the base stream from the distillation column and the base stream or part thereof, comprising methanol, water and methyl acetate is fed to the dehydration-hydrolysis reaction.

10. A process according to claim 1 wherein in step (b) the crude reaction product comprising acetic acid and dimethyl ether has a formic acid content of 500 ppm or less.

11. A process according to claim 2 wherein the methanol feed to step (I) comprises 50 to 99 mol % methanol and >0 to 1 mol % methyl formate.

12. A process according to claim 1 wherein the dehydration step (I) is carried out in the presence of at least one solid acid catalyst and wherein the at least one solid acid catalyst is a Brønsted acid catalyst selected from one or more of heteropolyacids and salts thereof and aluminosilicate zeolites.

13. A process according to claim 2 wherein dehydration step (I) is conducted as a vapour phase process.

14. A process according to claim 2 wherein the separation step (II) is carried out by distillation.

15. A process according to claim 14 wherein the distillation is carried out in a single distillation column which distillation column has at least 10 theoretical stages and is operated at a pressure of 5 to 30 barg and at a heads temperature of from 120 to 180° C.

16. A process according to claim 1 which further comprises step (a¹) in which at least a portion of the sidedraw stream withdrawn from the distillation column in step (a) and comprising methyl formate, dimethyl ether and one or more of methanol and water is supplied as feed to a further distillation column and distilled therein to withdraw from the distillation column a sidedraw stream enriched in methyl formate as compared to the feed mixture, a heads stream comprising dimethyl ether and a base stream comprising one or more of methanol and water.

17. A process according to claim 16 wherein the sidedraw stream comprises the majority of methyl formate present in the feed to the column and is withdrawn as a vapour stream.

18. A process according to claim 16 wherein the distillation column in step (a¹) is operated at 0.1 to 1 barg lower pressure than the distillation column of step (a).

19. A process according to claim 1 wherein the process is operated as a continuous process.

* * * * *